US00PP28607P3

(12) United States Plant Patent
Jacobs

(10) Patent No.: US PP28,607 P3
(45) Date of Patent: Nov. 7, 2017

(54) ***CHRYSANTHEMUM* PLANT NAMED 'ZANMUAVAL YELIMP'**

(50) Latin Name: ***Chrysanthemum×morifolium* Ramat.**
Varietal Denomination: Zanmuaval Yelimp

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 63 days.

(21) Appl. No.: 14/757,488

(22) Filed: Dec. 23, 2015

(65) Prior Publication Data

US 2017/0188501 P1 Jun. 29, 2017

(51) Int. Cl.
*A01H 5/02* (2006.01)

(52) U.S. Cl.
USPC ..... Plt./289

(58) Field of Classification Search
USPC ..... Plt./289, 287
See application file for complete search history.

*Primary Examiner* — June Hwu
(74) *Attorney, Agent, or Firm* — Steptoe & Johnson LLP

(57) ABSTRACT

A *chrysanthemum* plant named 'Zanmuaval Yelimp' characterized by its medium sized blooms with yellow ray florets and prolific branching; natural season flower date October 19; blooming for a period of 5 weeks.

3 Drawing Sheets

Botanical designation: *Chrysanthemum×morifolium* Ramat.

Cultivar denomination: 'Zanmuaval Yelimp'.

RELATED CULTIVARS

The new plant is a flower color mutant of 'Zanmuaval'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuaval Yelimp'. 'Zanmuaval Yelimp' is a product of a breeding and selection program which had the objective of finding flower color mutants from existing parent plants. The new plant comprises a whole plant mutant of the parent *chrysanthemum* named 'Zanmuaval' (U.S. Plant Pat. No. 22,659). Plants from the new cultivar 'Zanmuaval Yelimp' differ from plants of the female parent in the color of the ray-florets. The ray-florets of the parent are purple, while those of the new plant are yellow.

The new cultivar was discovered as a flower color mutant in May 2008 by Henricus Cornelius Maria Jacobs in a controlled environment (greenhouse) in Rijsenhout, the Netherlands. The first act of asexual reproduction of 'Zanmuaval Yelimp' was accomplished when after planting of the new plant as a motherplant in July 2008, vegetative cuttings from this 'Zanmuaval Yelimp' were taken and propagated further in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 22 weeks) is shown in the accompanying drawings, the color being as nearly true as possible with color photographs of this type.

DESCRIPTION OF THE INVENTION

Figure 1:
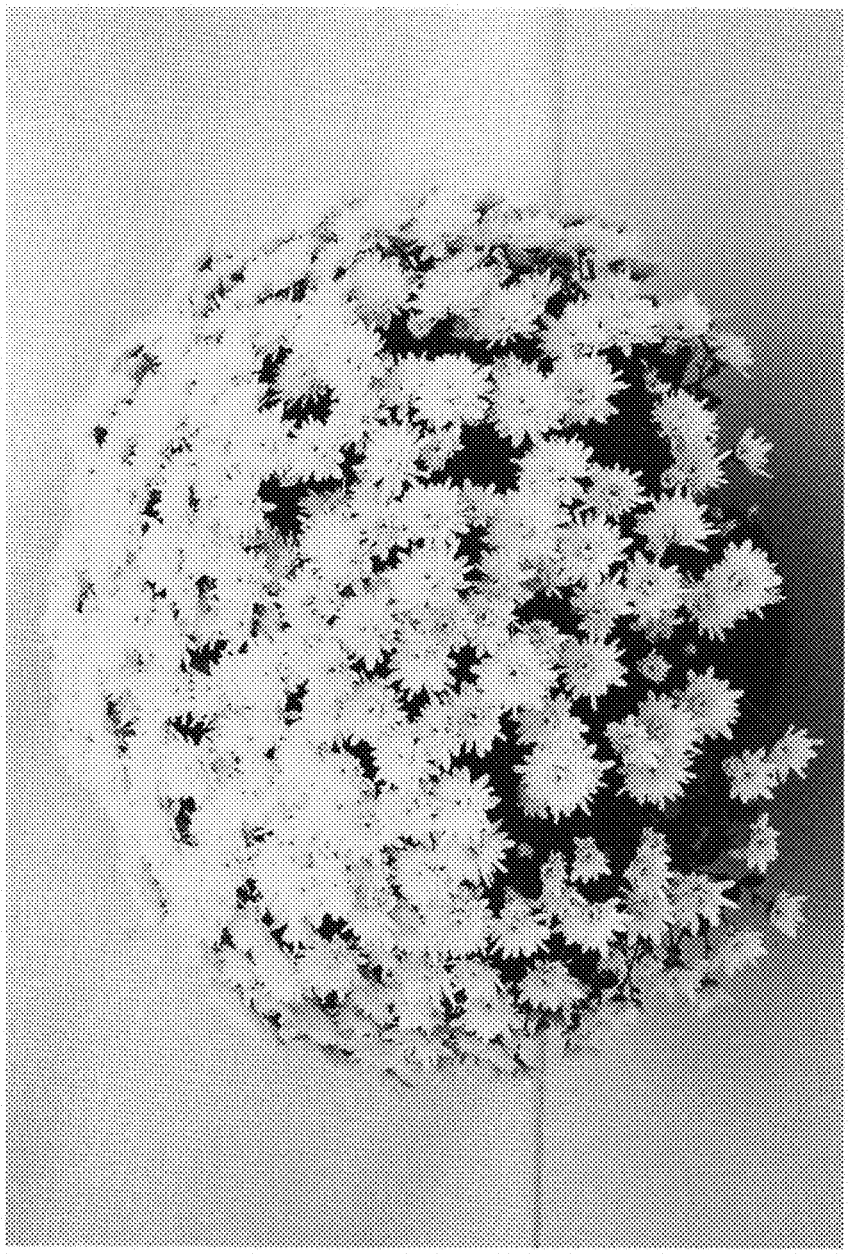
FIG. 1 shows a plant of the cultivar in full bloom.
Figure 2:
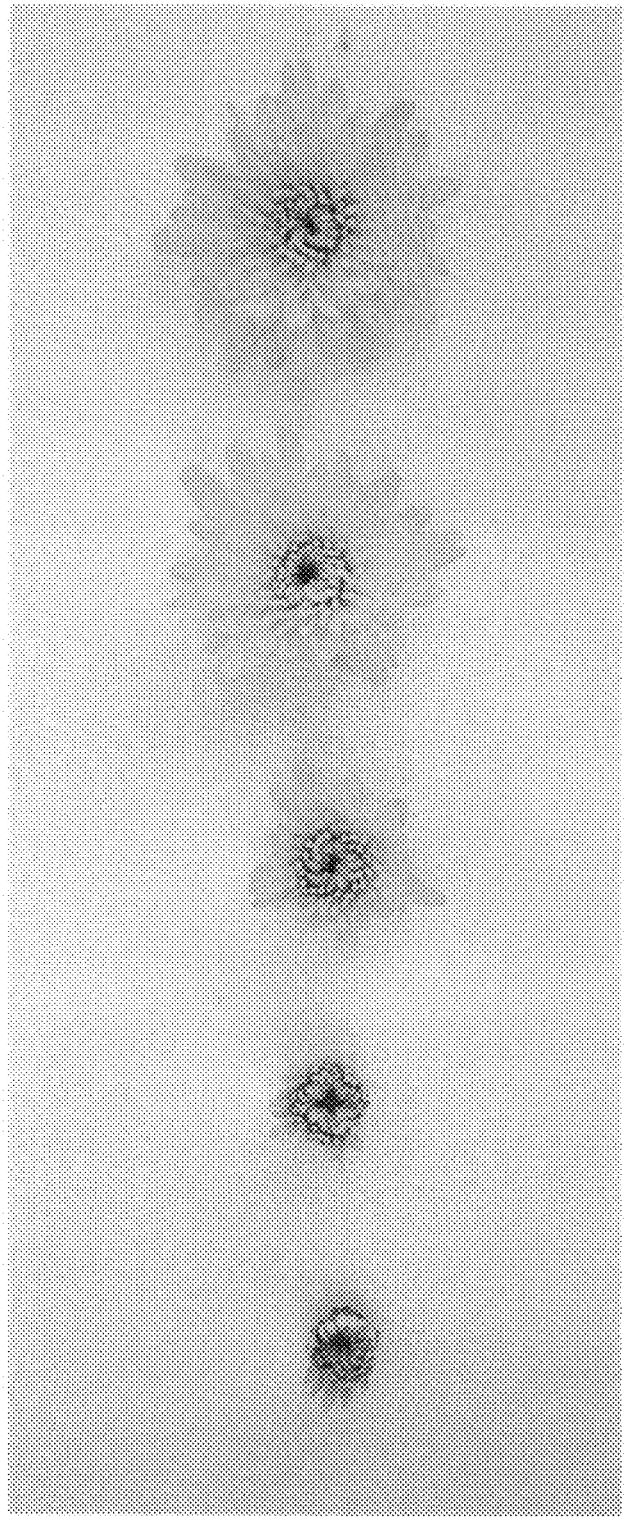
FIG. 2 shows the various stages of blooms of the new cultivar.
Figure 3:
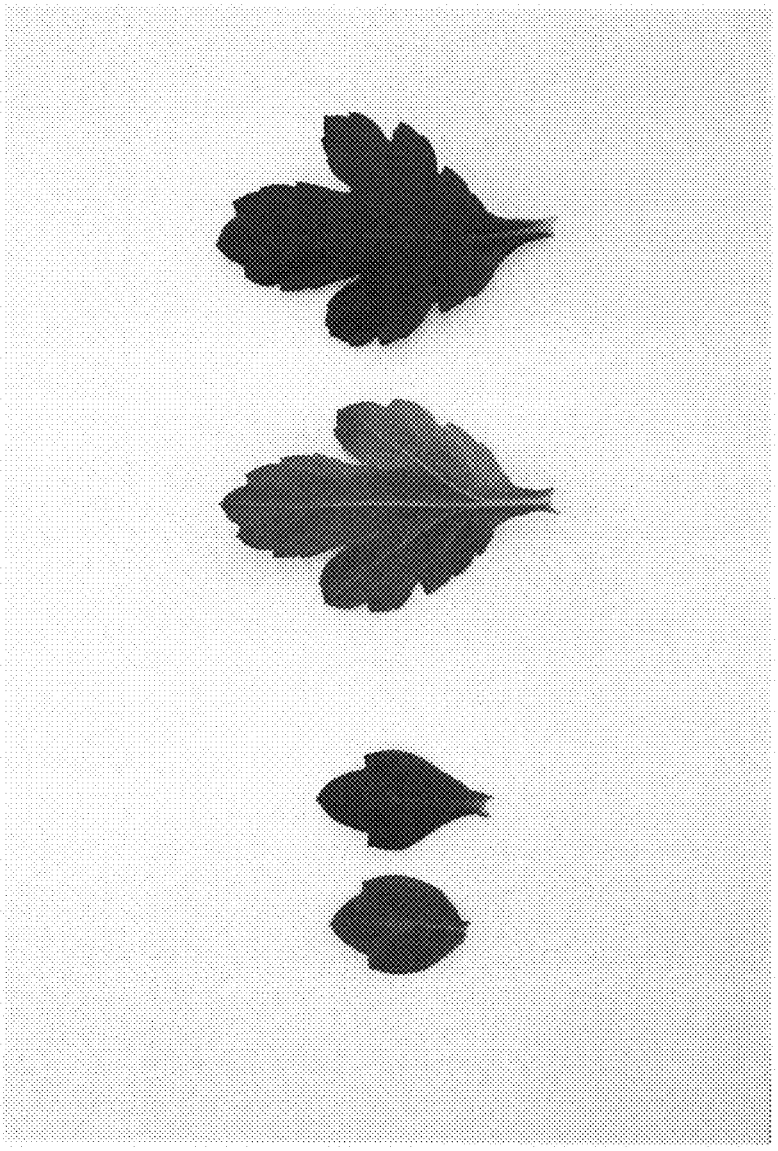
FIG. 3 shows the various stages of foliage of the new cultivar.

The observations and measurements were gathered from plants in the period of 21 to 26 weeks of age grown outdoor in Rijsenhout, the Netherlands, under natural day length and temperature and planted in week 23 in 2015. The natural blooming date of this crop was October 19 (week 43). The average height of the plants was 30 cm. No growth retardants were used. No tests were done on disease or insects resistance or susceptibility. No tests were done on cold or drought resistance. This new variety produces medium sized blooms with yellow ray florets and a greenish center blooming for a period of five weeks.

From the cultivars known to the inventor the most similar existing cultivar in comparison to 'Zanmuaval Yelimp' is 'Zanmuaval Golden' (U.S. Plant Pat. No. 24,020). When 'Zanmuaval Golden' and 'Zanmuaval Yelimp' are being compared the following differences are noticed: The differences of 'Zanmuaval Golden' and 'Zanmuaval Yelimp' are (1). Plant vigor. And (2). Ray-floret color. (1) Plants of 'Zanmuaval Golden' are more vigorous than those of 'Zanmuaval Yelimp'. (2) Ray-florets of 'Zanmuaval Golden' are more intensively yellow colored than those of 'Zanmuaval Yelimp'.

The following is a description of the plant and characteristics that distinguish 'Zanmuaval Yelimp' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, edition 2001.

TABLE 1

Botanical Description of *Chrysanthemum* × *morifolium* Ramat. 'Zanmuaval Yelimp'

| | |
|---|---|
| **Bud** | |
| Size: | Small; cross-section 5 mm, height 3 mm |
| Shape: | Round |
| Texture: | Pubescent |
| Outside color: | Greyed-green 191B |
| **Phyllaries** | |
| Number: | 18-20, arranged in 3 rows |
| Shape: | Elliptic |
| Apex: | Acute |
| Base: | Truncate |
| Margin: | Entire |
| Color: | Upper side: Greyed-green 191B<br>Lower side: Green 138A |
| Length and width: | 10 mm; 1 mm |
| Texture: | Pubescent |
| **Inflorescences** | |
| Type: | Double |
| Height: | 2.5 cm |
| Diameter: | 4.5 cm |
| Peduncle length: | 5-6 cm |
| Peduncle color: | Green 139C |
| Peduncle diameter: | 2 mm |
| Peduncle texture: | Pubescent |
| Peduncle strength: | Weak |
| Number per branch: | About 5-6 inflorescences |
| Duration of flowering: | 5 weeks |
| Seeds (after outcrossing): | Produced in small quantities, ovate, Greyed-brown 199A, length 1.5 mm, diameter 0.5 mm; texture: rough with ribs |
| Fragrance: | Faint chrysanthemum odor |
| **Color inflorescences** | |
| Center of inflorescence: | Yellow-green 150B |
| Color of upper side of ray florets: | Outer rows: Yellow 12A;<br>Inner rows: Yellow green 150B |
| Color of lower side of ray florets: | Outer rows: Yellow 10C;<br>Inner rows: Yellow-green 150B |
| Tonality from distance: | A garden mum with yellow blooms and a greenish center |
| Color of ray florets after aging of the plant: | Yellow 12B |
| **Ray florets** | |
| Number of types: | Two |
| Type: | Predominantly ligulate, few spatulate. |
| Texture: | Upper and lower side smooth |
| Number: | 180 to 200 |
| Shape: | Elliptic |
| Apex: | Dentate |
| Base: | Attenuate |
| Cross-section: | Flat |
| Longitudinal axis: | Straight |
| Length of corolla tube: | 2-3 mm |
| Diameter corolla tube: | 1 mm |
| Ray floret margin: | Entire |
| Ray floret length: | 0.8-2 cm |
| Ray-floret width: | 2-5 mm |
| Disc florets | Absent |
| **Receptacle** | |
| Color: | Yellow-green 145D |
| Shape: | Domed raised |
| Height: | 3 mm |
| Diameter: | 4 mm |
| **Reproductive Organs** | |
| Androecium: | Absent |
| Pollen: | Absent |
| Gynoecium: | Present on ray florets |
| Style color: | Yellow-green 154C |

TABLE 1-continued

Botanical Description of *Chrysanthemum* × *morifolium* Ramat. 'Zanmuaval Yelimp'

| | |
|---|---|
| Style length: | 4 mm |
| Stigma color: | Yellow 7A |
| Stigma width: | 1 mm |
| Ovary: | Enclosed in calyx |
| Ovary color: | Yellow-green 149D |
| **Plant** | |
| Type: | Bushy |
| Growth habit: | Spherical shape |
| Growth rate: | Medium |
| Height: | 30 cm |
| Width: | 45-50 cm |
| Stem color: | Greyed-brown 199A |
| Stem strength: | Weak |
| Stem brittleness: | Brittle |
| Stem anthocyanin coloration: | Not observed |
| Internode length: | 2 cm |
| Length of lateral branch: | From top to bottom 20 cm |
| Lateral branch color: | Green 138B |
| Lateral branch, attachment: | Weak |
| Lateral branch diameter: | 2 mm |
| Lateral branch texture: | Pubescent with ribs |
| Branching(average number of lateral branches): | Medium with 8-9 breaks after pinching |
| Natural season blooming date: | October 19 (week 43) in Rijsenhout, the Netherlands. |
| Root habits: | Fine, freely branching |
| Root color: | White 155D |
| Rooting time: | 6-8 days, formation rooted plants: 12-14 days |
| **Foliage** | |
| Leaf glossines: | Upper side: weak;<br>Lower side: very weak |
| Leaf color: | Upper side: Green 137A;<br>Lower side: Green 138A |
| Color midvein: | Upper side: Yellow-green 147D;<br>Lower side: Yellow-green 148D |
| Size: | Small; length 2.5-4 cm, width 1.8-3 cm |
| Quantity (number per lateral branches): | 12-14 |
| Shape: | Elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |
| Margin of sinus between lateral lobes: | Diverging |
| Shape of base: | Acute to truncate |
| Apex: | Mucronulate |
| Petiole attitude: | Moderately upwards |
| Petiole length: | 0.3-0.8 cm |
| Petiole diameter: | 2-4 mm |
| Petiole color: | Yellow-green 147D |
| Stipule: | Lacking |

TABLE 2

Differences with the comparison variety, when grown under identical conditions

| | 'Zanmuaval Yelimp' | 'Zanmuaval Golden' |
|---|---|---|
| Plant width | 45 cm | 50 cm |
| Ray-floret color | Yellow 12A | Yellow 13A |

I claim:

1. A new and distinct *chrysanthemum* plant named 'Zanmuaval Yelimp' as described and illustrated.

* * * * *